US00PP08575P

United States Patent [19]

Amador

[11] Patent Number: Plant 8,575

[45] Date of Patent: Feb. 1, 1994

[54] ALSTROEMERIA PLANT NAMED ALEXA

[75] Inventor: Julio Amador, Bogota, Colombia

[73] Assignee: Opal Resources Ltd., Panama, Panama

[21] Appl. No.: 979,579

[22] Filed: Nov. 20, 1992

[51] Int. Cl.[5] ..... A01H 5/00

[52] U.S. Cl. ..... Plt./87.1

[58] Field of Search ..... Plt. 87.1

*Primary Examiner*—James R. Feyrer
*Assistant Examiner*—Bruce R. Campbell
*Attorney, Agent, or Firm*—Christie, Parker & Hale

[57] ABSTRACT

A new and distinct Alstroemeria variety producing flowers comprising outer petals light purple (near 70B) with attractively contrasting white margins, and red-purple (near 71A) streaks mainly confined to margins but occasionally appearing in light purple area. Reverse side nearly uniform, near 70C to 70B. Inner petals similar with wider near 71A streaks and occasional yellow (near 4B) flush.

3 Drawing Sheets

BACKGROUND OF THE INVENTION

The present invention relates to a new and distinct cultivar of alstroemeria originated as a seedling of unknown parentage discovered among my collection of alstroemeria varieties maintained under controlled conditions in a greenhouse in Sabana de Bogota - Madrid (Cund), Colombia for developmental purposes. The new variety was selected from a mass planting of seeds resulting from undocumented crosses.

The first act of asexual reproduction of 'Alexa' was by propagation of vegetative cuttings in Bogota, Colombia. Asexual reproduction through successive generations has demonstrated that the combination of characteristics as herein disclosed for 'Alexa' are firmly fixed and retained through successive generations of asexual reproduction.

'Alexa' has not been observed under all possible environmental conditions. Phenotypic expression may vary significantly with variations in environment such as temperature, light intensity, day length and growing and cultural conditions.

SUMMARY OF THE INVENTION

Flowers of the new variety of alstroemeria, 'Alexa', are of the butterfly type and are larger than the variety 'Rosario', which is the closest known commercial cultivar. . 'Alexa' is characterized by a partial lilac coloration against a white background along its six elongated petals. The petals also display purple spots and streaks of light to dark coloration and of varying length. The inner petals are of a obvate-cuneate form with a central, very pale yellow portion which contrasts with the various purple tones. Most of the stems of the new variety have four long peduncles and flowers at the same time in its mature inflorescence. The new variety produces long, strong, flower bearing stems of excellent quality. It has been established that 'Alexa' may grow productively without need of shade and under greenhouse conditions. Moreover, the new variety has demonstrated a resistance to pests and diseases under greenhouse conditions.

DESCRIPTION OF ILLUSTRATIONS

The new variety of alstroemeria is illustrated in the accompanying illustrations which show typical inflorescence, foliage characteristics and plant base, of 'Alexa', with colors being as nearly true as possible for illustrations of this type.

DESCRIPTION OF THE NEW VARIETY

The following is a detailed description of the new cultivar of alstroemeria as observed during the month of August in a greenhouse in Bogota, Colombia at an elevation of 2400 meters above sea level. Color designations indicated are in accordance with The Royal Horticultural Society Colour Chart by color plate designations.

Botanical classification:
- *Family.*—Amaryllidaceae
- *Genus.*—Alstroemeria sp.

Origin: Seedling.

PLANT

Form: Parabolic.
Growth: Vigorous.
Branching: Floral stems proceed from subterraneous rhizomes.
Flower stem:
- *Length.*—About one meter.
- *Color.*—Near 183C.

Foliage:
- *Quantity.*—About 18 — Abundant.
- *Size of leaf.*—Length — About 100 mm. Width — About 30 mm.
- *Shape of leaf.*—Lanceolate.
- *Texture.*—Leaf top side — Bright, silky. Leaf underside — Easily corrugated.
- *Color.*—Leaf top side — Near 137B. Leaf underside — Near 137C.
- *Venation.*—Parallel veins — 8 main, 8 secondary disposed longitudinally.
- *Stem color.*—Near 138D.
- *Rhizomes.*—Color — Near 155A. Size — About 3 to 4 cm. in length.

BUD

Form (shape): Rhomboid at late stage, prior to opening.
Size: About 2 cm. in diameter, about 4 cm in length.
Calyx (shape): Absent; corolla/ovary juncture hexagonal in cross-section, with prominent nervures.
Opening rate: Average to 100% opening.

FLOWER

Blooming habit: Continuous.

Flower:

*Size.*—About 64 mm.

*Diameter.*—About 45 mm.

*Depth.*—Good.

*Borne.*—2 days for bud onset.

Inflorescence:

*Shape.*—Umbel of short, bud-forming racemes.

*Color.*—Near 70B when viewed from a distance.

Peduncle:

*Length.*—About 5 to 6 cm.

*Color.*—Near 138B.

*Diameter.*—About 3 mm.

*Approx. no. of flowers per stem.*—About 4.

Bloom:

*Type.*—Bell.

*Petalage.*—6 petals.

*Arrangement of petals.*—Typical of genus.

*Size (fully expanded).*—Outer petal — Long, about 70 mm×34 mm wide. Inner upper petal — About 67 mm long×19 mm wide. Inner lower petal — About 58 mm×18 mm.

*Shape.*—Outer — Heart shaped. Inner — Lanceolate.

*Texture of petals.*—Bright and smooth.

*Lasting quality after cutting.*—About 9 days.

Color:

*Flower coloration.*—Outer petals light purple (near 70B) with attractively contrasting white margins, and red-purple (71A) streaks mainly confined to margins but occasionally appearing in light purple area. Reverse side nearly uniform, 70C to 70B. Inner petals similar with wider 71A streaks and occasional yellow (near 4B) flush.

*Discoloration as bloom ages.*—Stable, slightly lighter than when fresh.

REPRODUCTIVE ORGANS

Stamens:

*Number.*—6.

Anthers:

*Size.*—About 7 mm.

*Color.*—Near 195A.

Filaments:

*Length.*—About 33 mm.

*Color.*—Near 74C.

Pollen:

*Color.*—Near 202A.

Pistils:

*Number.*—1.

*Styles.*—Length — About 25 mm. Color — Near 138D.

*Stigmas.*—Color — Near 74C.

Character of ovaries: Upper and lower.

I claim:

1. A new variety of Alstroemeria plant substantially as herein shown and described.

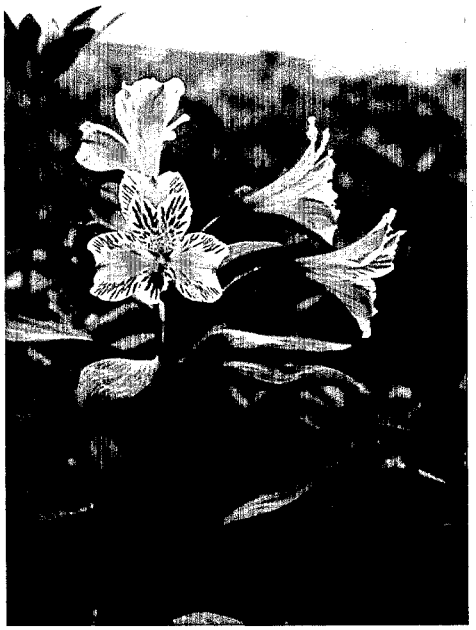

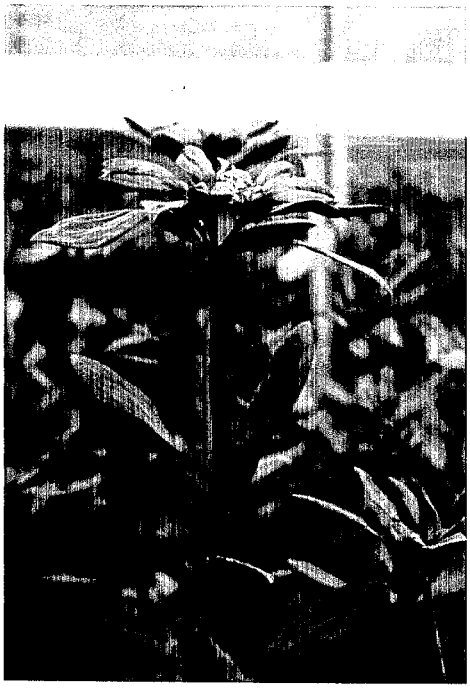

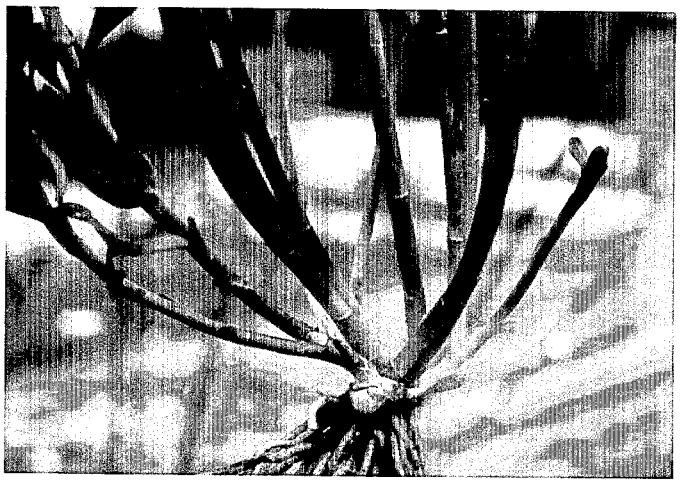

* * * * *